(12) United States Patent
Limodehi et al.

(10) Patent No.: US 10,527,539 B2
(45) Date of Patent: Jan. 7, 2020

(54) HUMIDITY SENSING SYSTEM AND METHOD

(71) Applicant: INSTITUT NATIONAL DE LA RECHERCHE SCIENTIFIQUE, Quebec (CA)

(72) Inventors: Hamid E. Limodehi, Côte Saint-Luc (CA); François Légaré, Saint-Eustache (CA); Mohamed Chaker, Montreal (CA)

(73) Assignee: Institut National de la Recherche Scientifique, Quebec (CA)

( * ) Notice: Subject to any disclaimer, the term of this patent is extended or adjusted under 35 U.S.C. 154(b) by 127 days.

(21) Appl. No.: 15/903,638

(22) Filed: Feb. 23, 2018

(65) Prior Publication Data

US 2018/0238791 A1    Aug. 23, 2018

Related U.S. Application Data

(60) Provisional application No. 62/462,565, filed on Feb. 23, 2017.

(51) Int. Cl.
*G01N 19/10* (2006.01)
*G02B 6/42* (2006.01)
(Continued)

(52) U.S. Cl.
CPC .......... *G01N 19/10* (2013.01); *G01D 5/353* (2013.01); *G01N 21/553* (2013.01);
(Continued)

(58) Field of Classification Search
CPC ................. G01N 21/553; G01N 2201/088
See application file for complete search history.

(56) References Cited

U.S. PATENT DOCUMENTS

| 2009/0262357 A1* | 10/2009 | Hofmann | G01N 21/553 356/448 |
| 2013/0011616 A1* | 1/2013 | Matsumura | G01N 21/554 428/148 |

(Continued)

FOREIGN PATENT DOCUMENTS

WO    9416312 A1    7/1994

OTHER PUBLICATIONS

Esmaeilzadeh et al., A super continuum characterized high-precision SPR fiber optic sensor for refractometry, Sensors and Actuators A 229 (2015) 8-14.

(Continued)

*Primary Examiner* — Tony Ko
(74) *Attorney, Agent, or Firm* — Lavery, De Billy, LLP; Hugh Mansfield

(57) ABSTRACT

A humidity sensing method and system comprising a transmitter, comprising a fiber optic head and a light source comprising a single LED emitting a measuring light, a receiver, and a sensing assembly comprising a plurality of optical fibers each comprising a first end fed the measuring light, a transducer positioned along a length thereof, the transducer comprising a side-polished portion of the optical fiber, the side polished portion coated with a gold layer and a film of a hydrophilic material wherein the transducer modifies an intensity of the measuring light dependent on an ambient humidity, and a second end for feeding the modified measuring light to the receiver, wherein the receiver compares an intensity of the measuring light with an intensity of the modified measuring light deriving therefrom a corresponding humidity level and dew point temperature.

24 Claims, 12 Drawing Sheets

(51) Int. Cl.
  *G01D 5/353* (2006.01)
  *G01N 21/552* (2014.01)
(52) U.S. Cl.
  CPC ..... *G02B 6/4246* (2013.01); *G01N 2201/088* (2013.01); *G02B 6/4298* (2013.01)

(56) References Cited

U.S. PATENT DOCUMENTS

2014/0186215 A1   7/2014  Shinta et al.
2018/0321150 A1*  11/2018 Gavaris ................ A61B 3/101

OTHER PUBLICATIONS

Esmaeilzadeh et al., Smart textile plasmonic fiber dew sensors, May 18, 2015, vol. 23, No. 10, DOI:10.1364/OE.23.014981, Optic Express 14981.
Iwami et al., Plasmon-resonance dew condensation sensor made of gold-ceramic nanocomposite and its application in condensation prevention, Sensors and Actuators B 184 (2013) 301-305.
Popov et al., Measurement of surface dew by optical sensor, Sensors and Actuators A 51 (1996) 199-202.
Rivero et al., Optical fiber humidity sensors based on localized surface plasmon resonance (LSPR) and lossy-mode resonance (LMR) in overlays loaded with silver nanoparticles, Sensors and Actuators B 173 (2012) 244-249.

* cited by examiner

HUMIDITY SENSING SYSTEM AND METHOD

CROSS REFERENCE TO RELATED APPLICATIONS

This Application claims priority under 35 USC § 119(e) of U.S. provisional application Ser. No. 62/462,565 filed on Feb. 23, 2017. All documents above are incorporated herein in their entirely by reference.

FIELD OF THE INVENTION

The present invention relates to a humidity sensing system and method. In particular, the present invention relates to a distributed optical dew and humidity sensing system.

BACKGROUND

Dew and humidity monitoring is essential to prevent potentially catastrophic consequences in advanced industries such as oil and gas, petrochemical, semiconductor manufacturing, food and beverages, pharmaceuticals, lithium battery manufacturing, and gas-insulated high-voltage equipment. Furthermore, dew monitoring is required in various drying and heat treatment processes such as plastic molding and metal treatment, as well as in compressed air pipelines to prevent ice formation, equipment corrosion, and poor end-product quality.

There are currently a number of dew and humidity sensors on the market. The most common variety is sensors with electrical probes, which operate by measuring the change in certain electrical parameters, such as capacitance or resistance. Alternatively, there exist optical dew and humidity sensors, which function by measuring the reflection or refraction of light by either a chilled mirror or an optical waveguide through a free-space optical set up. Further, studies have been conducted regarding the use of fiber optic sensors to measure humidity and moisture. Such sensors operate by methods such as direct spectroscopy, evanescent waves, in-fiber grating, interferometry, or a combination of these methods.

The dew and humidity sensors currently available have several drawbacks. These sensors are not suitable for operation in hazardous or combustible locations, are not immune to electromagnetic interference, and are not small enough to be used in remote or difficult to access locations. Therefore, there exists a need for a dew and humidity sensor that meets these criteria as well as being of low cost, easy to operate, easy to maintain, and providing for remote, parallel and distributive operation.

SUMMARY OF THE INVENTION

In order to address the above and other drawbacks, there is provided a method for sensing humidity within a wet area comprising placing a plurality of transducers about the wet area, each of the transducers comprising a side-polished portion of a respective one of an optical fiber coated with a gold layer and a film of a hydrophilic material, transmitting a measuring light emitted by a single LED through each of the transducers, the transducer modifying an intensity of the measuring light dependent on a thickness of a water layer on the polished portion, and determining a difference in intensity between the measuring light and the modified measuring light wherein a sensed humidity is inversely proportional to the difference.

There is also provided a humidity sensing system comprising a transmitter, comprising a fiber optic head and a light source comprising a single LED emitting a measuring light, a receiver, and a sensing assembly comprising a plurality of optical fibers each comprising a first end fed the measuring light, a transducer positioned along a length thereof, the transducer comprising a side-polished portion of the optical fiber, the side polished portion coated with a gold layer and a film of a hydrophilic material wherein the transducer modifies an intensity of the measuring light dependent on an ambient humidity, and a second end for feeding the modified measuring light to the receiver, wherein the receiver compares an intensity of the measuring light with an intensity of the modified measuring light deriving therefrom a corresponding humidity level and dew point temperature.

Additionally there is provided a method for sensing humidity within a wet area comprising placing at least one transducer within the wet area, the at least one transducer comprising a side-polished portion of a respective one of an optical fiber coated with a gold layer and a film of a hydrophilic material, reducing a temperature of the at least one transducer within the wet area while transmitting a measuring light through the at least one transducer, the at least one transducer modifying an intensity of the measuring light dependent on a thickness of a water layer on the polished portion, and measuring the modified intensity, wherein the modified intensity changes at a rate relative to the humidity in the wet area.

Also, there is provided a method for sensing changes in humidity within a wet area over a period of time comprising placing at least one transducer within the wet area, the at least one transducer comprising a side-polished portion of a respective one of an optical fiber coated with a gold layer and a film of a hydrophilic material, alternately reducing and increasing a temperature of the at least one transducer during the period of time about a dew point $T_{dew}$ while transmitting a measuring light through the transducer, the transducer modifying an intensity of the measuring light dependent on a thickness of a water layer on the polished portion, and measuring the modified intensity during the time period, wherein the modified intensity changes at a rate relative to the humidity in the wet area.

DETAILED DESCRIPTION OF THE ILLUSTRATIVE EMBODIMENTS

Figure 1:
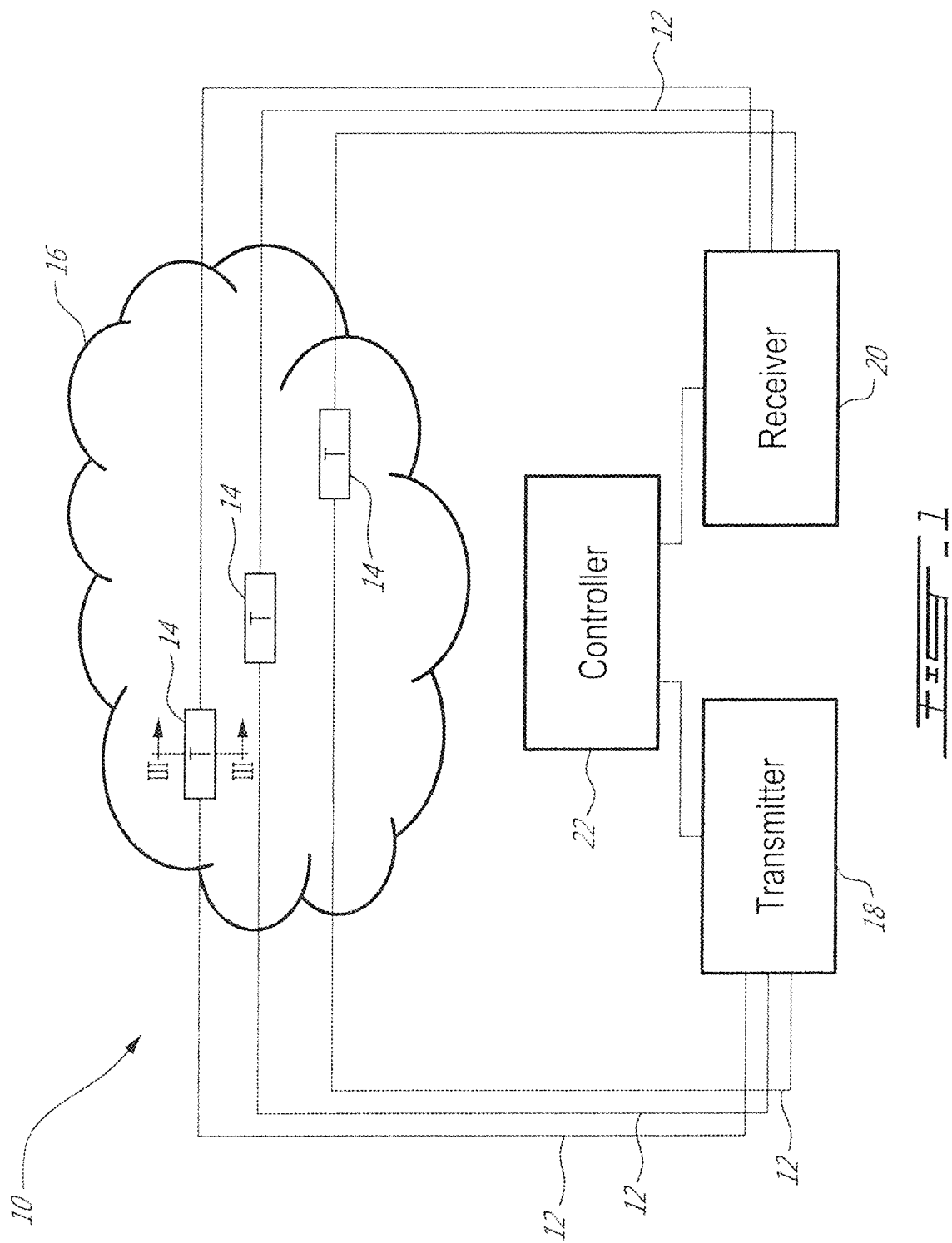
FIG. 1 provides a schematic diagram of a distributed optical dew and humidity sensing system in accordance with an illustrative embodiment of the present invention.

Referring now to FIG. 1, a humidity sensing system, generally referred to using the reference numeral 10, will now be described. The system comprises a plurality of optical fibers 12, each comprising a transducer 14 positioned along a length thereof. Each optical fiber 12 is connected to a transmitter 18 at one end and a receiver 20 at another end. The transmitter 18 and receiver 20 are connected to and under the control of a controller 22. The transducers are situated inside a wet area 16 whose dew point temperature and humidity level are to be measured. To do so, as will be discussed in further detail below, light is transferred from the transmitter 18 to the receiver 20 via the optical fibers 12 and is modified at the transducers 14 inside the wet area 16.

Figure 2:
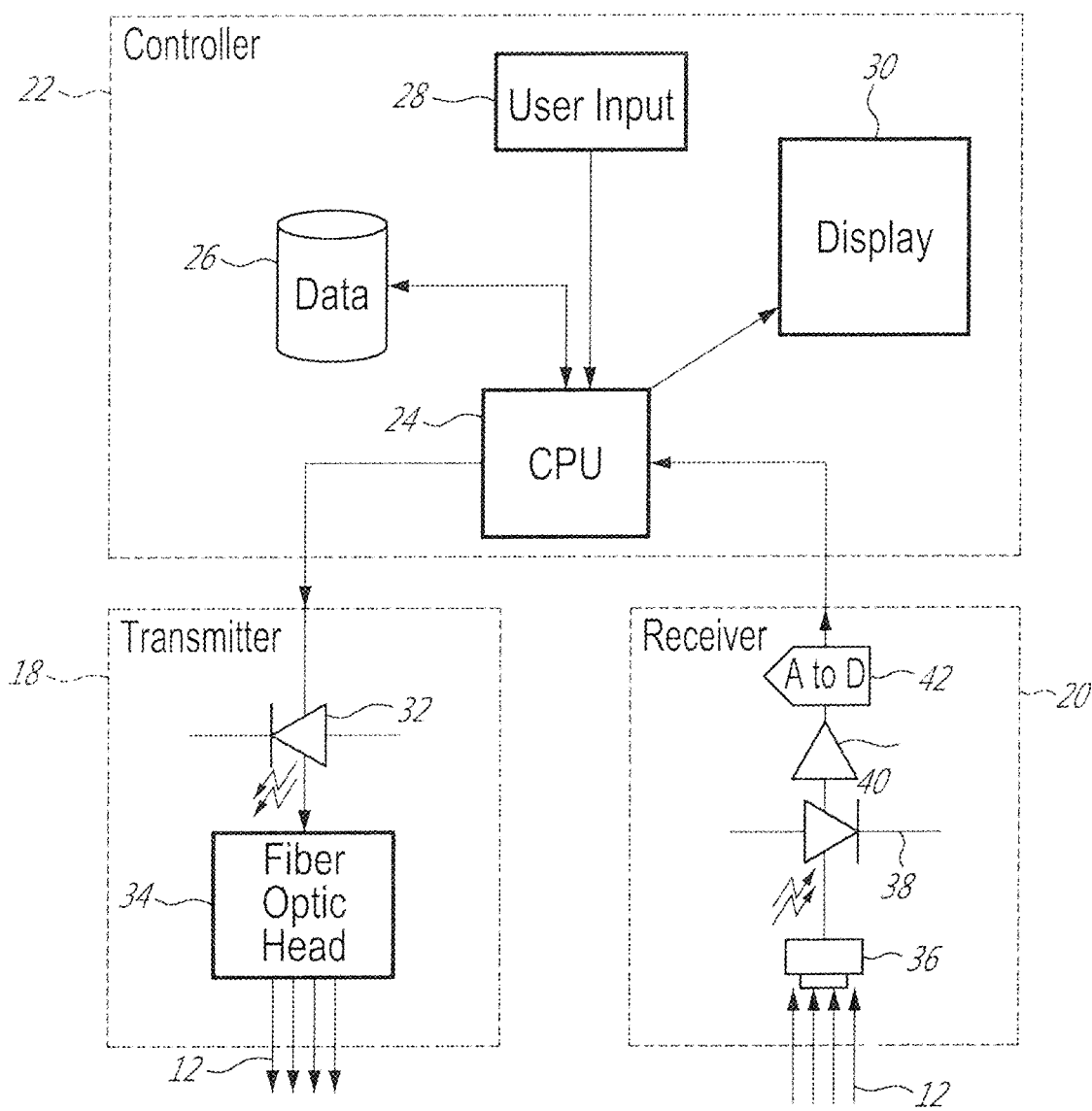
FIG. 2 provides a schematic diagram of a transmitter, receiver and controller in accordance with an illustrative embodiment of the present invention.

Referring now to FIG. 2 in addition to FIG. 1, the controller 22 comprises a microcontroller (CPU) 24, a data store 26, a user input 28 and a display 30. The transmitter 18 comprises a light source 32, illustratively a single red LED, and a fiber optic head 34 connected to the plurality of optical fibers 12. The receiver 20 comprises a Fiber Channel Angled Physical Contact (FC/APC) mating sleeve 36, a photoconductive cell 38, illustratively a cadmium sulfide photoconductive cell, an amplifier 40, illustratively with a voltage signal gain of 6 V/mV, and an analog to digital (A to D) converter 42, illustratively a 16-bit analog to digital converter.

Still referring to FIG. 2 in addition to FIG. 1, in an illustrative embodiment, a user would use the user input 28 to activate the light source 32 via the CPU 24. The light source would then feed a measuring light (not shown) into the fiber optic head 34 for transmission along the plurality of optical fibers 12. The measuring light would then be modified via the transducers 14, discussed in further detail below, before returning via the plurality of optical fibers 12 to the receiver 20 at the FC/APC mating sleeve 36 by a FC/APC type connector (not shown). The optical power of the received measuring light, illustratively measured in microwatts, would then be converted into an electrical signal, illustratively DC voltage, using the photoconductive cell 38, the electrical signal then amplified by the amplifier 40. The amplified electrical signal is then converted into a digital signal using the A to D converter 42, the newly converted digital signal sent back to the CPU 24 for analysis, the results of which would appear on the display 30 and be stored in the data store 26 for further comparison and analysis purposes.

Figure 3:
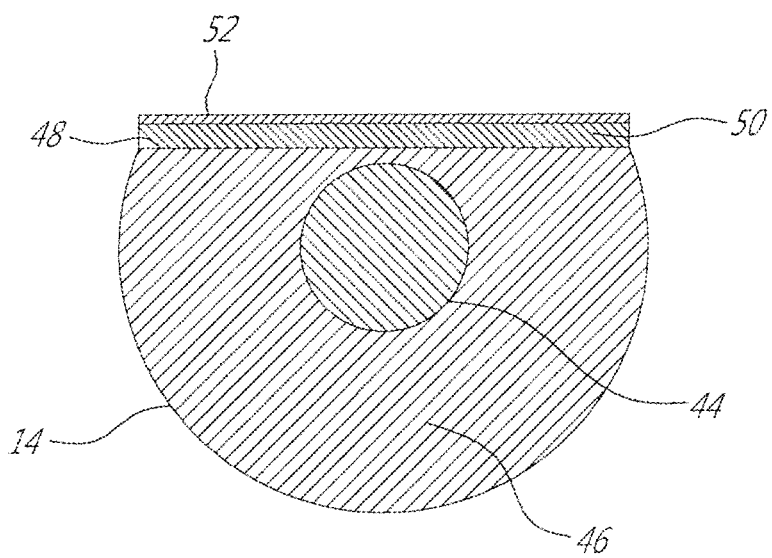
FIG. 3 provides a cross sectional view of a fiber optic transducer in accordance with an illustrative embodiment of the present invention.

Referring now to FIG. 3 in addition to FIG. 1, each fiber optic transducer 14 portion of each optical fiber 12 comprises a core 44, cladding 46, and a side polished portion 48. The side polished portion 48 is coated in a 45 nm gold layer 50, illustratively using a DC sputtering method at room temperature, and in a 5 nm film of Hexamethyldisilazane 52, illustratively using a spray method in an oven at 110 degrees Celsius, giving the side polished portion hydrophilic characteristics.

Still referring to FIG. 3 in addition to FIG. 1, when the measuring light passes through the optical fibers 12 to each transducer 14, surface plasmon waves on the side polished portion 48 of each transducer 14 are excited due to condensation of water vapor (not shown) in air adjacent to the surface, resulting in the formation of a thin layer of water (dew) on the surface of the side polished portion 48 of each transducer 14. The intensity of the measuring light is modified as it passes through each transducer 14. This modification, discussed in further detail below, is directly related to the change in thickness of the layer of water due to evaporation or condensation on the surface of the side polished portion 48 of each transducer 14. The modified measuring light is then fed through the plurality of optical fibers 12 until it reaches the receiver 20 to be processed, as discussed above. The receiver 20 is capable of multi-channel detection and monitoring, allowing for simultaneous parallel measurements to be recorded and compared at different locations inside the wet area 16.

Still referring to FIG. 3 in addition to FIG. 1, each transducer 14 is sensitive to changes in the refractive index of the environment adjacent to the surface of the side polished portion 48 of each transducer 14. As moisture forms on the surface of the side polished portion 48 of each transducer 14, the optical power of the measuring light passing through each transducer 14 is reduced due to Surface Plasmon Resonance (SPR) loss resulting from the condensation of water vapor on the side polished portion 48 of each transducer 14 from the surrounding wet area 16. Similarly, the optical power of the measuring light is increased due to SPR gain as a result of the evaporation of water from the side polished portion 48 of each transducer 14 to the surrounding wet area 16. The intensity of the modified measuring light is then compared to the initial intensity of the transmitted measuring light to determine the humidity level. In a first embodiment, humidity levels are measured by analyzing the inverse relationship between humidity level and the optical power of the modified measuring light. In a second embodiment, humidity is measured by analyzing the proportional relationship between humidity level and the falling or rising rate of the optical power of the modified measuring light.

Figure 4:
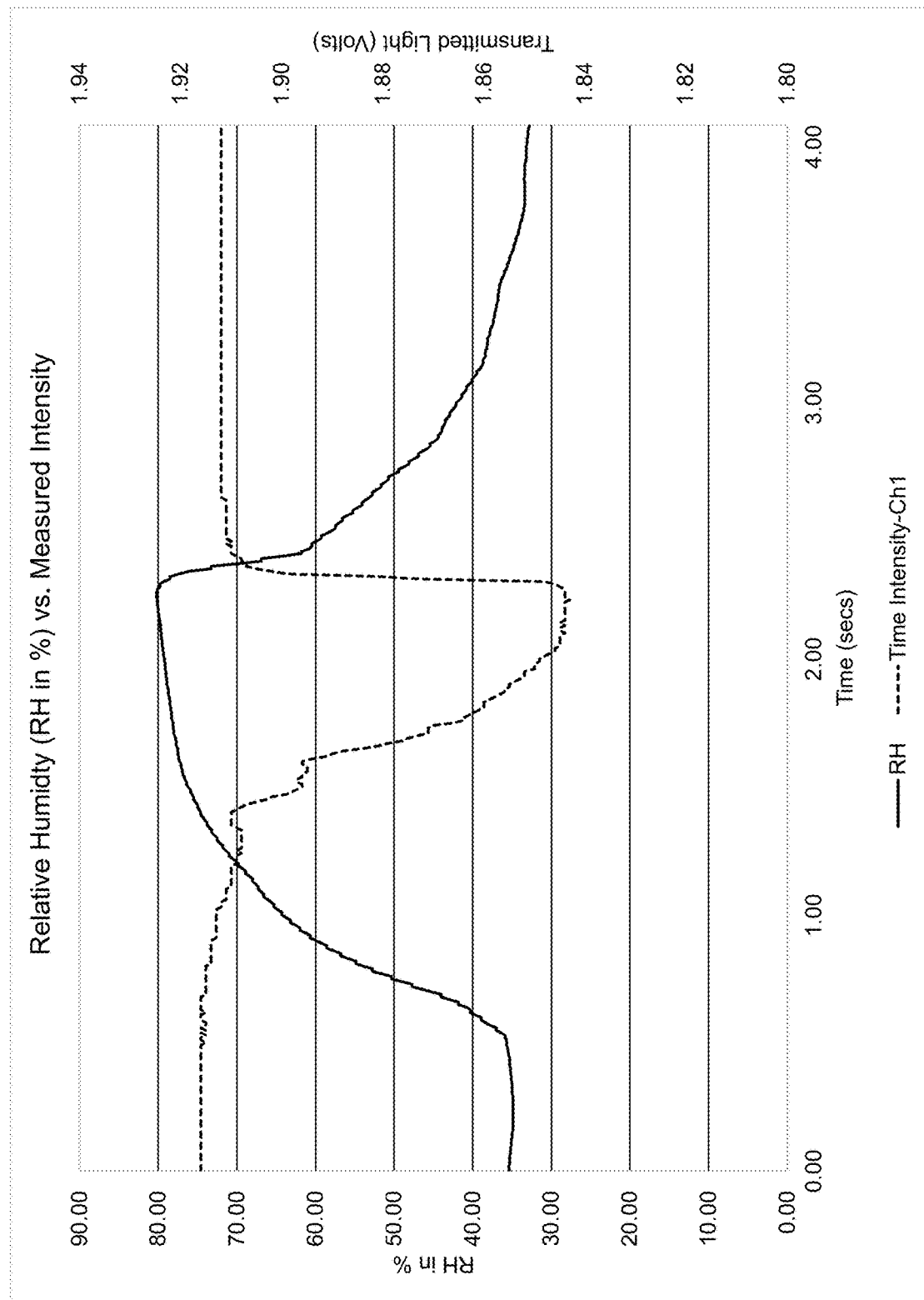
FIG. 4 provides a graph illustrating the relationship between transmitted light intensity and relative humidity in accordance with an illustrative embodiment of the present invention.

Referring to FIG. 4, the system is illustratively foreseen implementing one of two approaches for measuring ambient humidity. In a first approach the fiber optic transducer is directly exposed to moisture in an ambient gas such as air, allowing small droplets of liquid such as water vapor, suspended in the gas, to come into contact with the transducer 14. This causes a decrease in the intensity of the optical signal (light) which is transmitted between the transmitter 18 and receiver 20 via the transducer 14 which is inversely proportional to the level of humidity/moisture. A typical transmitted light versus ambient humidity is provided in FIG. 4.

$$\text{Intensity} \propto \frac{1}{\text{Relative Humidity}} \quad (1)$$

Figure 5:
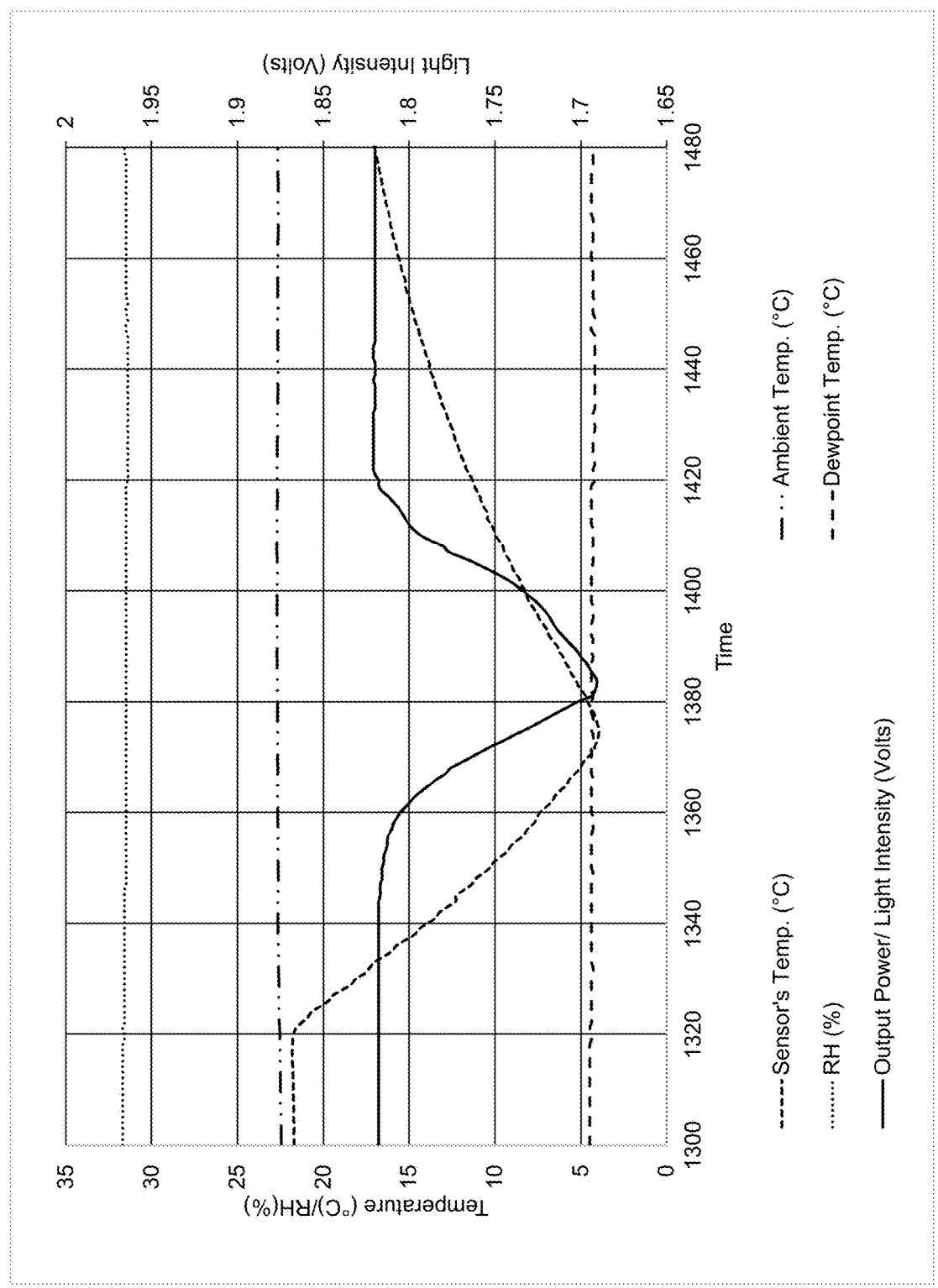
FIG. 5 provides a graph illustrating the effect of condensation and evaporation on transmitted light intensity in accordance with an illustrative embodiment of the present invention.

Referring now to FIG. 5, in a second approach of measuring the ambient humidity the ambient dew point temperature ($T_{dew}$) is first determined. In order to determine $T_{dew}$ the temperature of each transducer 14 is illustratively lowered below that of the ambient temperature, for example using a Peltier thermoelectric cooler (not shown), and until a thin measurable layer of water is formed on the surface of the transducer 14, which provides an indication that $T_{dew}$ has been reached. In this regard, the refractive index of the medium immediately adjacent the transducer 14 is changed from 1 to approximately 1.33 at $T_{dew}$, causing surface plasmon resonance and a corresponding decrease in the power of the light transmitted via the transducer 14. When a temperature of the transducer 14 is reached which gives rise to relatively large decrease in the optical power of the modified measuring light, $T_{dew}$ is identified. The cooler can be switched off allowing the temperature of the transducer 14 to increase back to the ambient temperature. This second approach can itself be used in two different methods.

In a first method, an analysis of the proportional relationship between moisture and the rate of increasing or decreasing optical power of the modified measuring light is applied. In this regard, it is known that as the surrounding environment becomes warmer and dryer the rate of moisture formation on a solid surface slows. As a result, the rate of water vapor condensation on a solid surface depends largely on the ambient relatively humidity. During condensation, the free energy of the water molecules from the air is absorbed by the solid surface because of the phase shift from gas to liquid. The condensation rate on the surface $\dot{m}$ can be calculated using the following equation, a combination of Incropera and Magnus formula:

$$\dot{m} = \frac{h_{eff} A_s}{h_{fg}} \left[ \frac{243.04\left[\ln\left(\frac{RH}{100}\right) + \frac{17.62T}{243.04+T}\right]}{17.62 - \ln\left(\frac{RH}{100}\right) + \frac{17.62T}{243.04+T}} - T_s \right] \quad (2)$$

where $h_{eff}$ is the effective heat transfer coefficient, $A_s$ is the surface area exposed to the ambient water vapor, $T_{dew}$ is the ambient dew point temperature, $T_s$ is the surface (or sensor) temperature, and $h_{fg}$ is the specific enthalpy of the saturated vapor. The constant values used in the formula should slightly be corrected empirically depend to the ambient conditions.

Figure 6A:
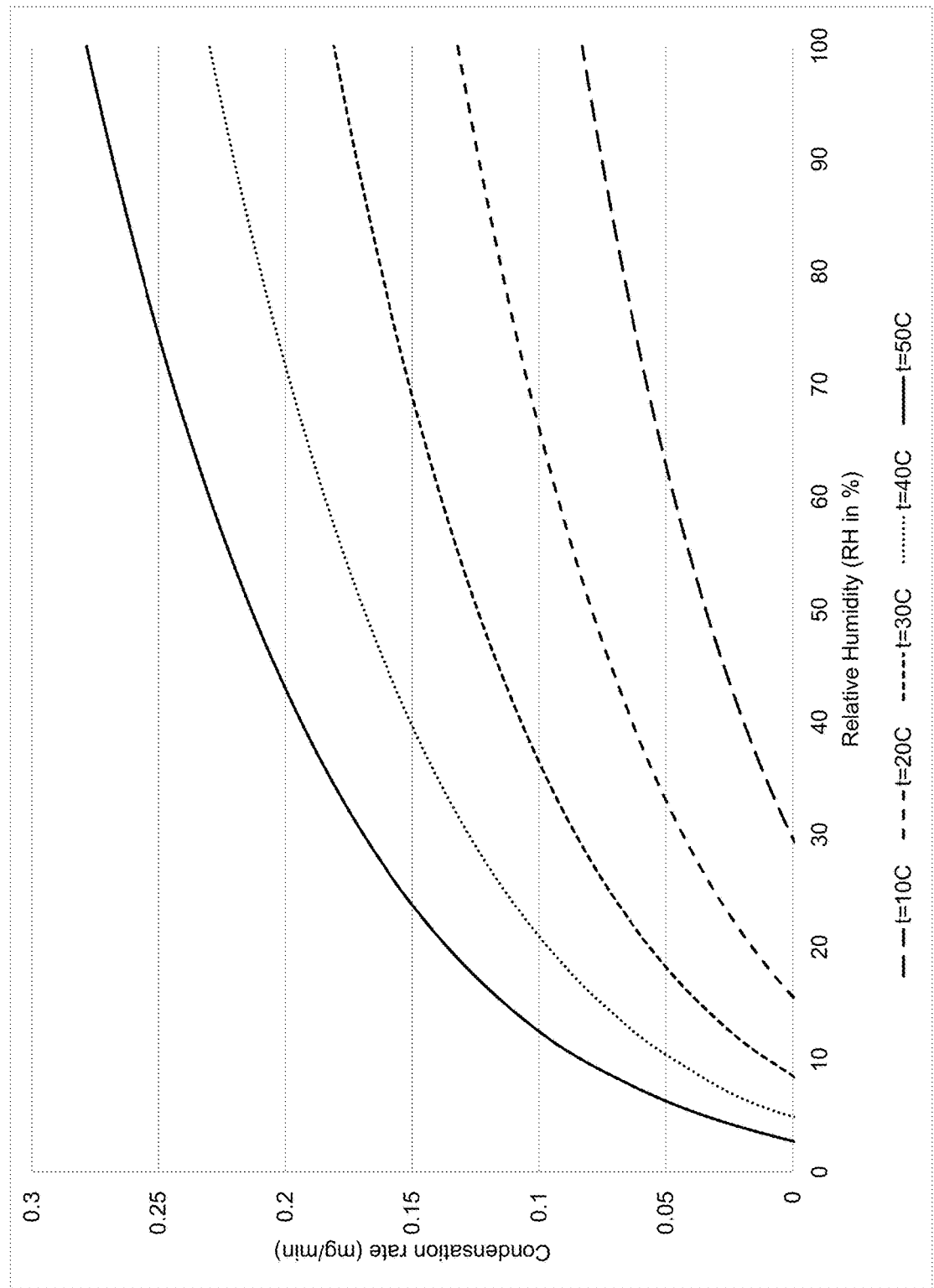
FIG. 6A provides a graph illustrating the relationship between relative humidity and condensation rate at various transducer temperatures in accordance with an illustrative embodiment of the present invention.
Figure 6B:
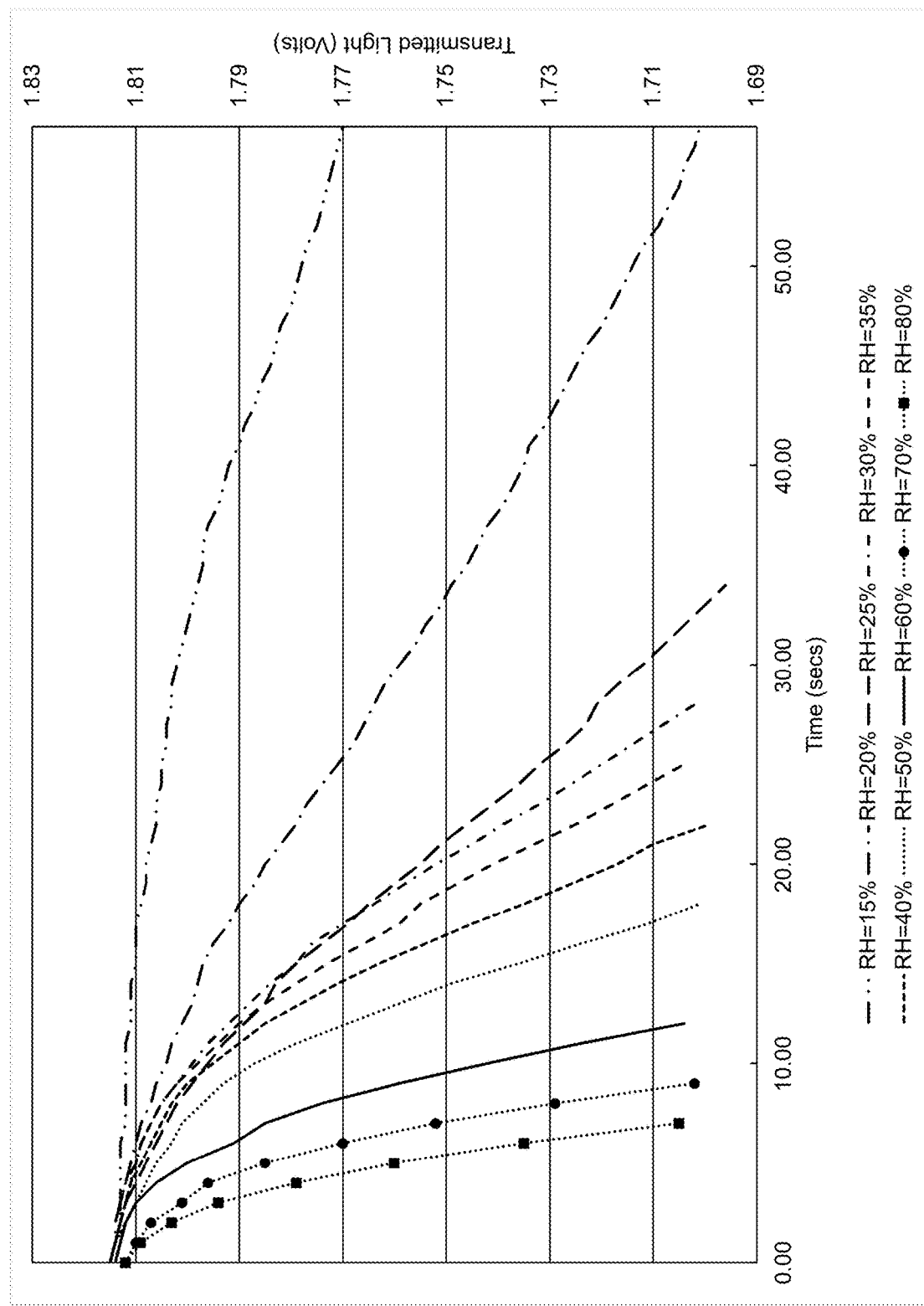
FIG. 6B provides a graph illustrating the dependence of transmitted light intensity decrease to ambient relative humidity during condensation and in accordance with an illustrative embodiment of the present invention.
Figure 6C:
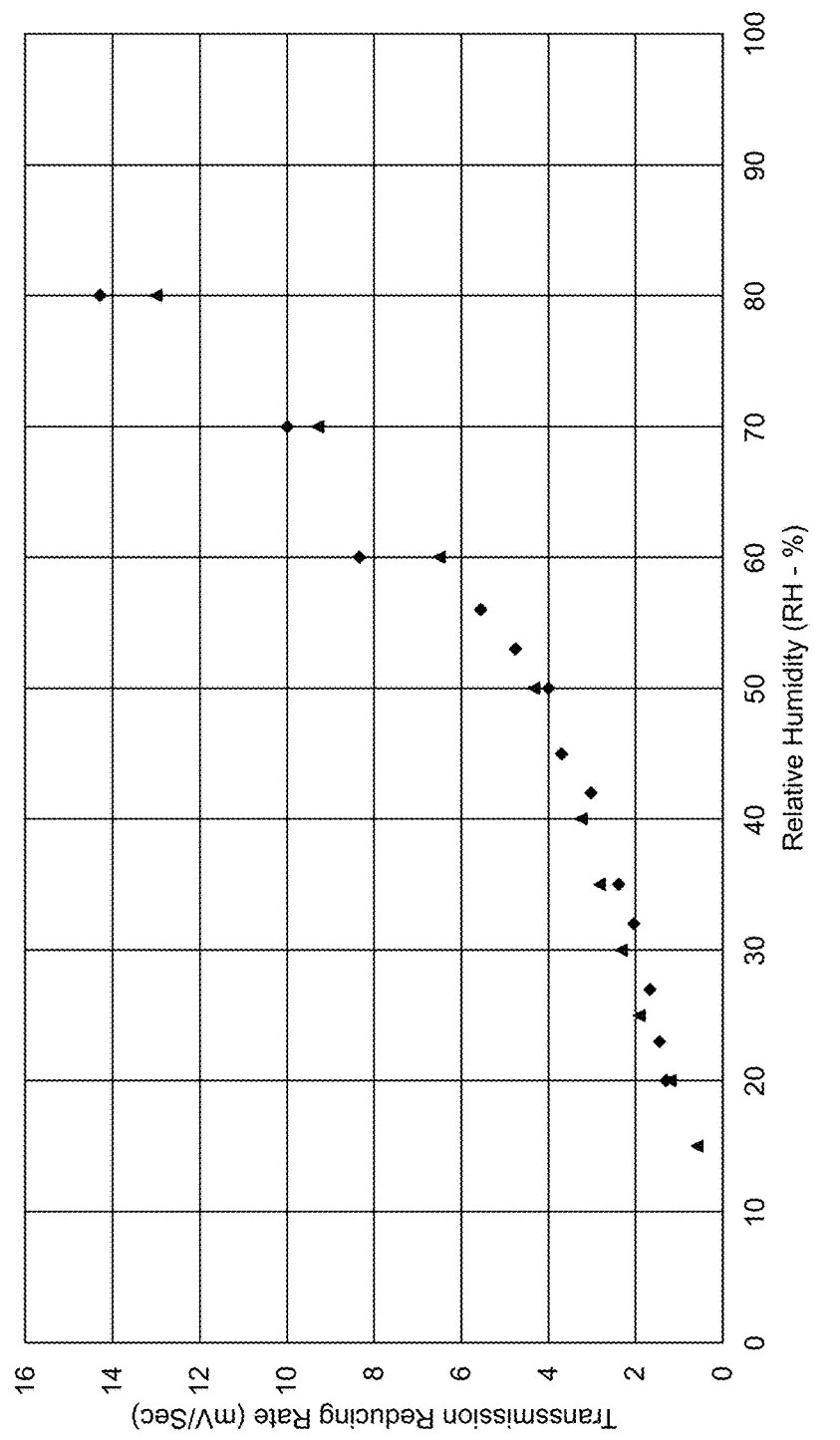
FIG. 6C provides a graph illustrating the relationship between a reducing rate of transmitted light intensity and relative humidity at different ambient temperatures in accordance with an illustrative embodiment of the present invention.

Referring to FIG. 6A, a theoretical rate of water vapor condensation versus relative humidity at various temperatures is provided. As shown, the greater the ambient relative humidity, the greater the condensation rate. Referring to FIG. 6B, experimental results demonstrate that the transmitted light intensity decreases faster when the ambient relative humidity is higher, as suggested by the theoretical values of FIG. 6A. FIG. 6C provides the relationship between the transmission reduction rate and ambient relative humidity during moisture formation.

Figure 7A:
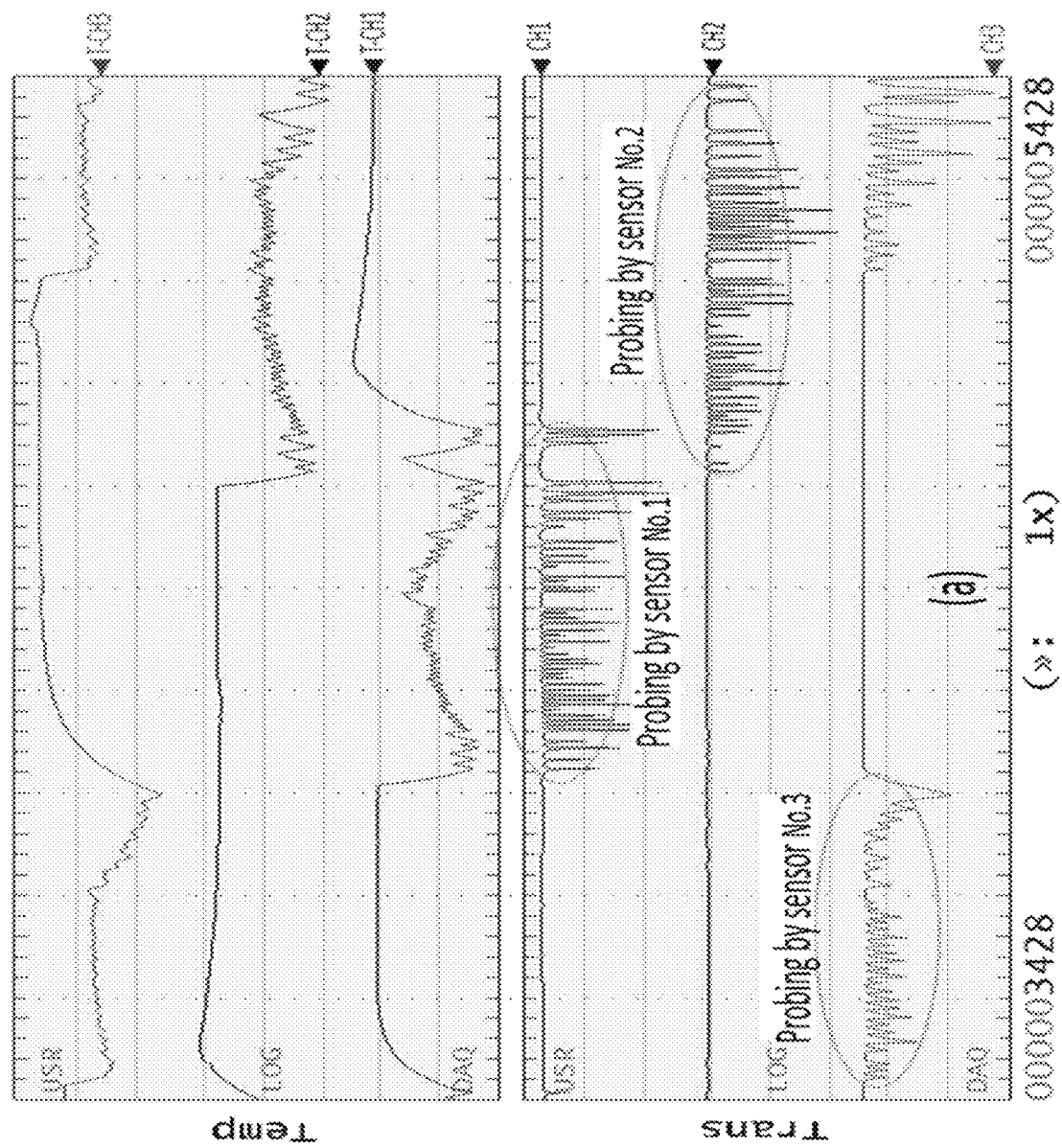
FIG. 7A provides measured outputs of light intensity and transducer temperature over a time period for three different transducers in accordance with an illustrative embodiment of the present invention.

In a second method, referred to as the scrolling method, the temperature of the transducer ($T_s$) is either lowered (for example by a Peltier thermo-electric cooler, not shown) or raised during ambient humidity variation until the ambient dew point ($T_{dew}$) is reached. Illustratively, the cooling and heating effect is applied with a frequency of between 0.1 Hz and 1 Hz. In one embodiment the described scrolling method is applied to a multi-channel fiber optic dew and humidity sensor (MODHS) with three operating channels, comprising three transducers 14 each situated in a separate chamber with ambient temperatures of circa 22° C. in all chambers. The "scrolling" temperature are displayed in upper plot of FIG. 7A. The corresponding transmission light intensities are also displayed in the bottom of FIG. 7A which show the probing procedure for each channel.

Figure 7B:
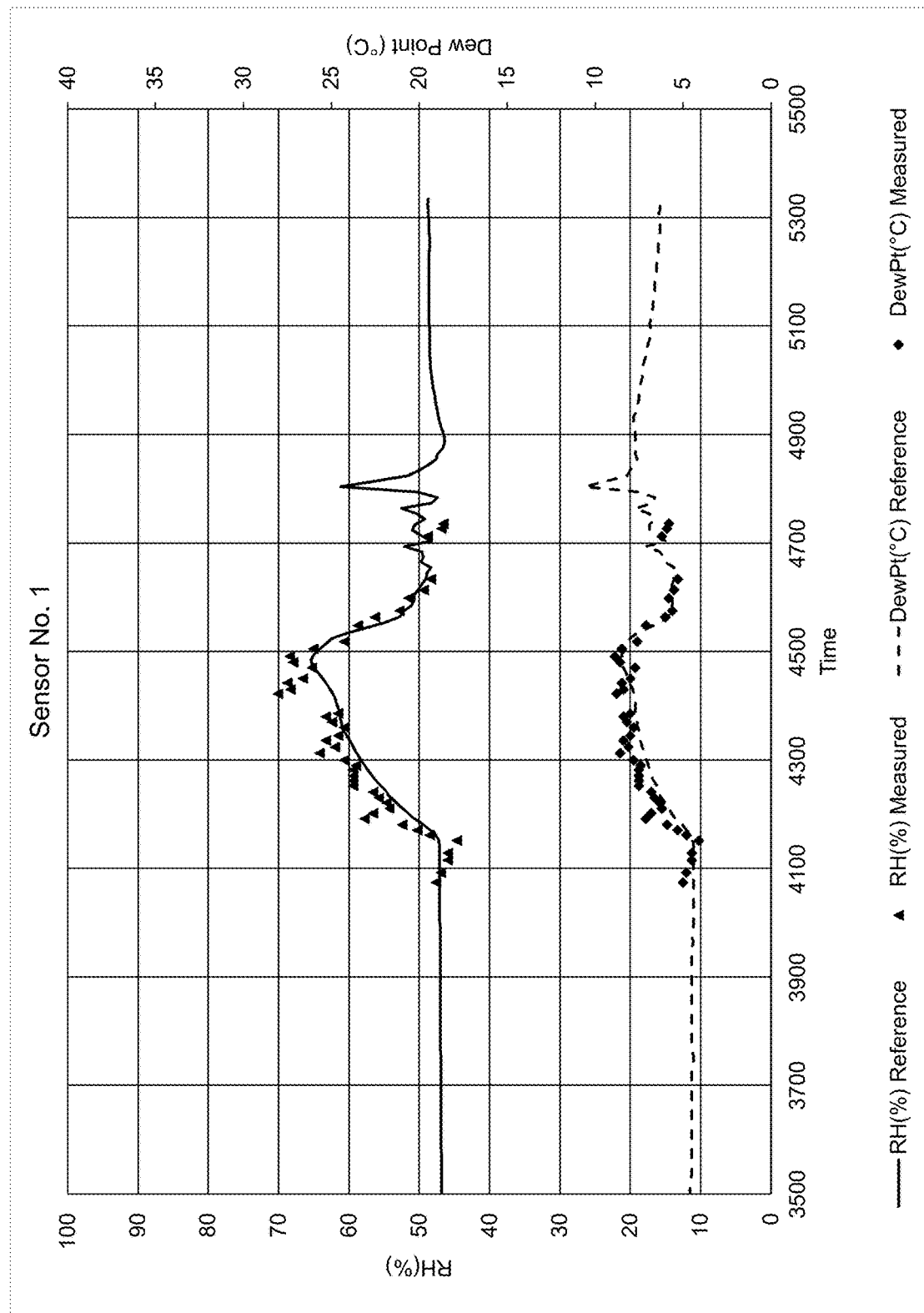
FIGS. 7B, 7C and 7D provide values for relative humidity and dew point over a time period, measured respectively by a first, second and third transducer versus reference values and in accordance with an illustrative embodiment of the present invention.
Figure 7C:
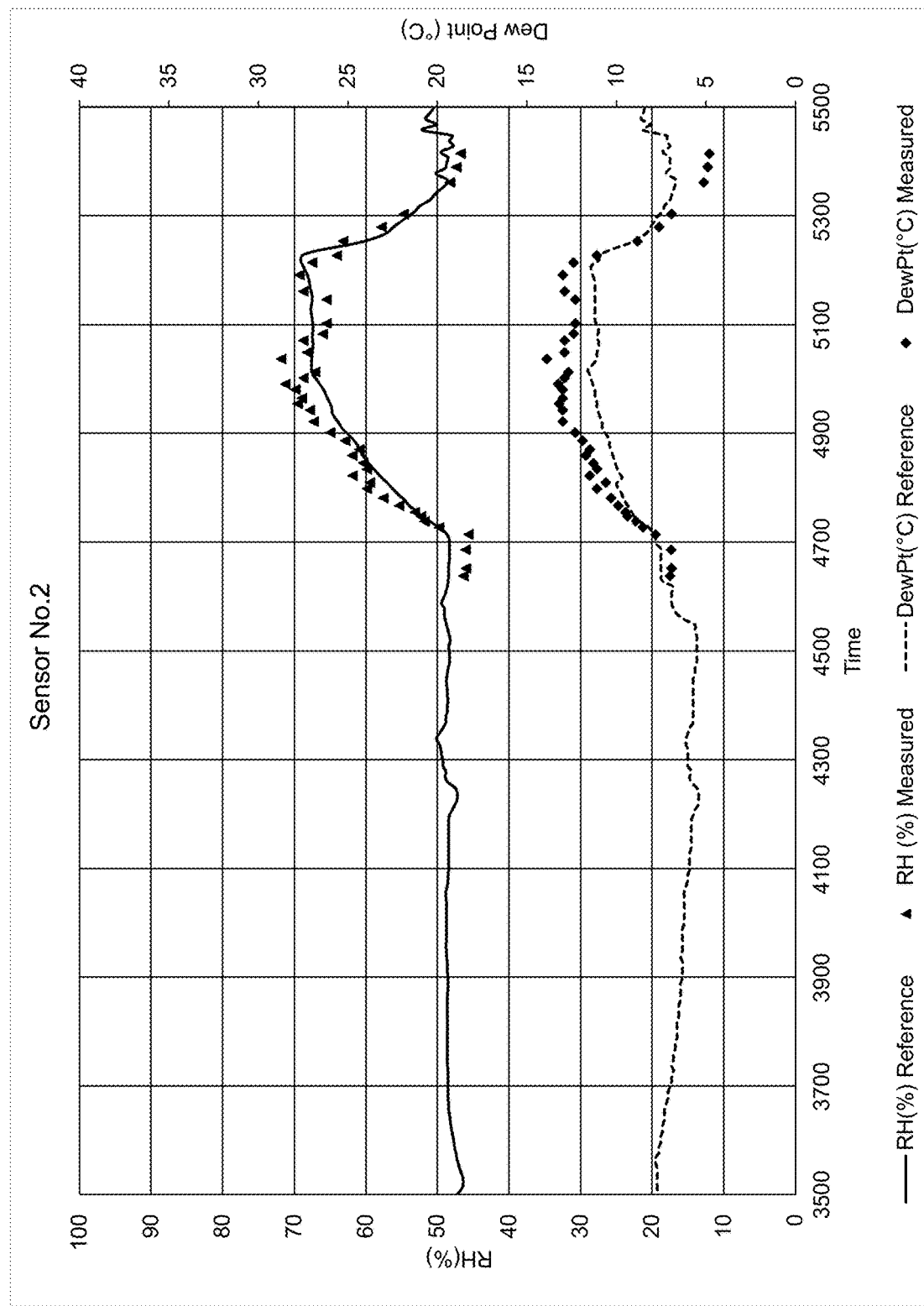
Figure 7D:
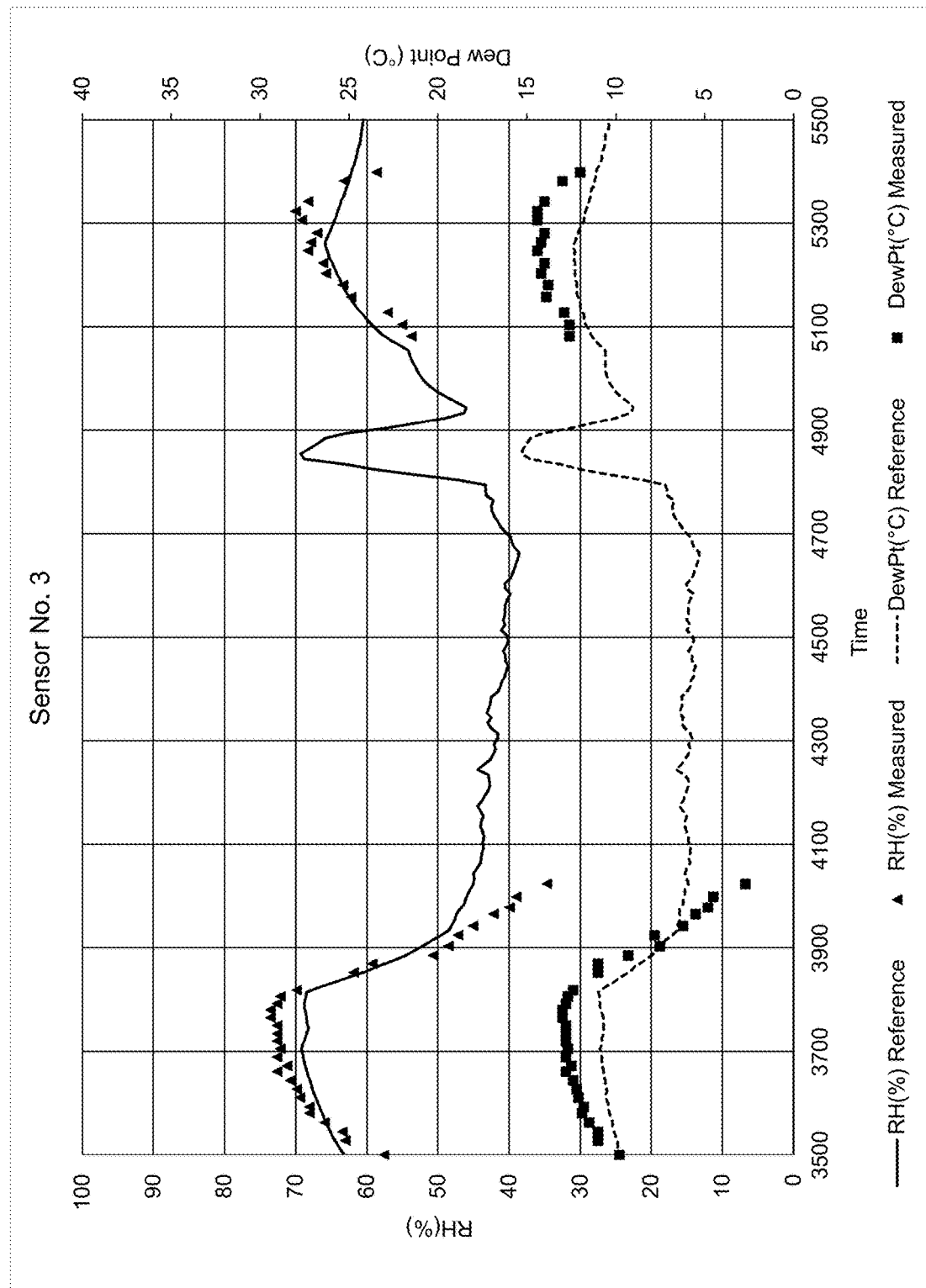

To illustratively investigate their performance, each chamber is shown respectively in FIGS. 7B, 7C and 7D. Values of the ambient dew point $T_{dew}$ and relative humidity acquired by the system 10 are plotted together with values measured by reference sensors (not shown).

The results provided in FIGS. 7B, 7C and 7D confirm the interrelation of $T_{dew}$ and RH for the all three channels. The system allows the simultaneous measurement of the relative humidity and dew point $T_{dew}$ for different environments even this with unstable or fast changing condition.

Although the disclosed measurements were carried out in a relative humidity range of between 10% to 80%, using the scrolling method the system would work in a wider ambient relative humidity range.

Although the present invention has been described hereinabove by way of specific embodiments thereof, it can be modified, without departing from the spirit and nature of the subject invention as defined in the claims.

We claim:

1. A method for sensing humidity within a wet area comprising:
   placing a plurality of transducers about the wet area, each of said transducers comprising a side-polished portion of a respective one of an optical fiber coated with a gold layer and a film of a hydrophilic material;
   transmitting a measuring light emitted by a single LED through each of said transducers, said transducer modifying an intensity of said measuring light dependent on a thickness of a water layer on said polished portion; and
   determining a difference in intensity between said measuring light and said modified measuring light wherein a sensed humidity is inversely proportional to said difference.

2. The method of claim 1, comprising prior to said transmitting, establishing a constant K and further wherein said sensed humidity is proportional to said difference according to the equation sensed humidity=K/difference.

3. A humidity sensing system, comprising:
   a transmitter, comprising a fiber optic head and a light source comprising a single LED emitting a measuring light;
   a receiver; and
   a sensing assembly comprising a plurality of optical fibers each comprising a first end fed said measuring light, a transducer positioned along a length thereof, said transducer comprising a side-polished portion of said optical fiber, said side polished portion coated with a gold layer and a film of a hydrophilic material wherein said transducer modifies an intensity of said measuring light dependent on an ambient humidity, and a second end for feeding said modified measuring light to said receiver;
   wherein said receiver compares an intensity of said measuring light with an intensity of said modified measuring light deriving therefrom a corresponding humidity level and dew point temperature.

4. The humidity sensing system of claim 3, wherein said thickness of said layer of water varies by condensation and evaporation dependent on ambient conditions, temperature and humidity in the environment adjacent to said transducers and a resulting surface plasmon resonance loss in said measuring light.

5. The humidity sensing system of claim 3, wherein the thickness of said gold layer is 45 nm.

6. The humidity sensing system of claim 3, wherein the thickness of said film of a hydrophilic material is 5 nm.

7. The humidity sensing system of claim 3, wherein the colour of said single LED is red.

8. The humidity system of claim 3, wherein said receiver comprises a detecting module and a display for multi-channel detection and monitoring purposes.

9. The humidity system of claim 3, wherein said hydrophilic material comprises Hexamethyldisilazane.

10. The humidity system of claim 3, wherein said sensing assembly comprises three optical fibers.

11. The humidity system of claim 3, wherein said transducer modifies an intensity of said measuring light dependent on a thickness of a layer of water on said polished portion.

12. The humidity system of claim 3, wherein each of said transducer further comprises a cooler.

13. The humidity system of claim 12, wherein said cooler comprises a Peltier effect device.

14. A method for sensing humidity within a wet area comprising:
placing at least one transducer within the wet area, said at least one transducer comprising a side-polished portion of a respective one of an optical fiber coated with a gold layer and a film of a hydrophilic material;
reducing a temperature of said at least one transducer within the wet area while transmitting a measuring light through said at least one transducer, said at least one transducer modifying an intensity of said measuring light dependent on a thickness of a water layer on said polished portion; and
measuring said modified intensity, wherein said modified intensity changes at a rate relative to the humidity in the wet area.

15. The method of claim 14, wherein said reducing a temperature comprises cooling said at least one transducer to a dew point $T_{dew}$ in the wet area.

16. The method of claim 14, wherein said reducing a temperature comprises cooling said at least one transducer using a Peltier effect device.

17. The method of claim 14, comprising, prior to said reducing a temperature, establishing a relationship between humidity and said rate.

18. The method of claim 14, wherein said rate increases with an increase in humidity.

19. The method of claim 14, wherein said placing comprises placing a plurality of transducers within the wet area.

20. The method of claim 14, comprising alternately reducing and increasing a temperature of said at least one transducer during the period of time while transmitting a measuring light through said transducer.

21. The method of claim 20, wherein said increasing a temperature comprises halting cooling of said at least one transducer and such that said transducer increases towards an ambient temperature.

22. The method of claim 20, wherein said alternating is carried out at a frequency of between 0.1 and 1 Hz.

23. The method of claim 20, wherein said increasing comprises heating said at least one transducer towards an ambient temperature using a Peltier effect device.

24. The method of claim 14, further comprising during the time period displaying the humidity in the wet area.

* * * * *